US010213182B2

(12) United States Patent
Millett

(10) Patent No.: US 10,213,182 B2
(45) Date of Patent: Feb. 26, 2019

(54) DEVICES, SYSTEMS, AND METHODS FOR ASSESSING A VESSEL UTILIZING ANGLED FLOW-SENSING ELEMENTS

(71) Applicant: Volcano Corporation, San Diego, CA (US)

(72) Inventor: Bret C. Millett, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 146 days.

(21) Appl. No.: 14/663,093

(22) Filed: Mar. 19, 2015

(65) Prior Publication Data
US 2015/0272538 A1  Oct. 1, 2015

Related U.S. Application Data

(60) Provisional application No. 61/970,762, filed on Mar. 26, 2014.

(51) Int. Cl.
*A61B 8/06* (2006.01)
*A61B 8/08* (2006.01)
(Continued)

(52) U.S. Cl.
CPC ............... *A61B 8/06* (2013.01); *A61B 5/026* (2013.01); *A61B 5/02007* (2013.01); *A61B 5/0215* (2013.01); *A61B 8/12* (2013.01); *A61B 8/488* (2013.01); *A61B 5/742* (2013.01); *A61B 8/4461* (2013.01)

(58) Field of Classification Search
CPC .. A61B 8/06; A61B 8/12; A61B 8/488; A61B 5/02007; A61B 5/026; A61B 5/0215; A61B 5/742
See application file for complete search history.

(56) References Cited

U.S. PATENT DOCUMENTS 4,733,669 A * 3/1988 Segal .................. A61B 5/6886
600/465
5,655,537 A   8/1997 Crowley
(Continued)

FOREIGN PATENT DOCUMENTS

| JP | 10328188 A | 12/1998 |
|---|---|---|
| JP | 2013-116332 | 6/2012 |
| WO | 2009105616 A2 | 8/2009 |

OTHER PUBLICATIONS

International Search Report and the Written Opinion received in Patent Cooperation Treaty Application No. PCT/US2015/022013, dated Jun. 29, 2015, 13 pages.

*Primary Examiner* — Mark W Bockelman

(57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries by monitoring fluid flow. In some embodiments, the devices, systems, and methods of the present disclosure include a flow-sensing element within a distal portion of an intravascular device that is mounted at an oblique angle with respect to a central longitudinal axis of the intravascular device. The angled flow-sensing element can be oriented away from a vessel wall and towards the center of the vessel lumen through rotation of the intravascular device.

12 Claims, 8 Drawing Sheets

(51) Int. Cl.
A61B 5/02 (2006.01)
A61B 5/026 (2006.01)
A61B 5/00 (2006.01)
A61B 8/12 (2006.01)
A61B 5/0215 (2006.01)
A61B 8/00 (2006.01)

(56) References Cited

U.S. PATENT DOCUMENTS

| | | | |
|---|---|---|---|
| 6,129,672 A * | 10/2000 | Seward | A61B 8/06 |
| | | | 128/916 |
| 6,955,675 B2 * | 10/2005 | Jain | A61B 18/1492 |
| | | | 606/41 |
| 7,930,014 B2 | 4/2011 | Huennekens et al. | |
| 8,277,386 B2 | 10/2012 | Ahmed | |
| 2005/0215946 A1 * | 9/2005 | Hansmann | A61B 5/027 |
| | | | 604/66 |
| 2008/0275335 A1 | 11/2008 | Zhang et al. | |
| 2012/0123271 A1 * | 5/2012 | Cai | A61B 8/06 |
| | | | 600/454 |
| 2012/0277592 A1 | 11/2012 | Zelenka | |
| 2013/0137985 A1 * | 5/2013 | Ho | A61B 8/4494 |
| | | | 600/445 |
| 2013/0303907 A1 | 11/2013 | Corl | |
| 2013/0303920 A1 * | 11/2013 | Corl | A61B 8/12 |
| | | | 600/468 |

* cited by examiner

DEVICES, SYSTEMS, AND METHODS FOR ASSESSING A VESSEL UTILIZING ANGLED FLOW-SENSING ELEMENTS

CROSS REFERENCE TO RELATED APPLICATIONS

The present application claims priority to and the benefit of the U.S. Provisional Patent Application Nos. 61/970,762 filed Mar. 26, 2014 which is hereby incorporated by reference in their entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

One currently accepted technique for assessing the severity of a stenosis in a blood vessel is coronary flow reserve (CFR). CFR is a measure for determining whether a stenosis is functionally significant. CFR can be calculated as a ratio of the hyperemic average peak velocity of blood flow to the baseline (resting) average peak velocity. Instantaneous peak velocity (IPV) is the peak observed velocity for an instantaneous Doppler spectrum provided by a Doppler transducer. An exemplary method of calculating an average peak velocity (APV) comprises averaging a set of IPV's over a cardiac cycle. A normal CFR is greater than about 2 and indicates that a lesion is not significant. Lower values may require intervention. CFR may be measured prior to treatment to determine if treatment is required and may be used post-treatment to determine the efficacy of treatment.

Another currently accepted technique for assessing the severity of a stenosis in a blood vessel is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting. Some intravascular devices incorporate a combination of sensing elements suitable for measuring both pressure and flow within a vessel, such that FFR and CFR measurements can be made.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries with flow-sensing elements.

SUMMARY

Embodiments of the present disclosure are configured to assess the severity of a blockage in a vessel and, in particular, a stenosis in a blood vessel utilizing an intravascular device having a flow-sensing element mounted within a distal portion of an intravascular device at an oblique angle with respect to a central longitudinal axis of the intravascular device. In that regard, the angled flow-sensing element can be oriented away from a vessel wall and towards the center of the vessel lumen through rotation of the intravascular device to facilitate better flow measurements.

In some instances, a flow-sensing intravascular device is provided that includes a flexible elongate member having a proximal portion, a distal portion, and a central longitudinal axis, the flexible elongate member sized and shaped for insertion into human vasculature; and a flow sensing element fixedly secured to the distal portion of the flexible elongate member, wherein the flow sensing element is mounted at an oblique angle with respect to the central longitudinal axis of the flexible elongate member. The oblique angle can be any suitable angle, including between about 10 degrees and about 60 degrees, and between about 20 degrees and about 40 degrees. In some instances, the flow sensing element is an ultrasound transducer, such as an ultrasound transducer configured to detect Doppler shifts in blood flow. The ultrasound transducer is mounted at a distal tip of the flexible elongate member in some instances. A connector is coupled to the proximal portion of the flexible elongate member and in communication with the flow sensing element in some implementations. The flexible elongate member has an outer diameter of approximately 0.014" in some instances.

In some instances, a system is provided that includes a flow-sensing intravascular device that comprises a flexible elongate member having a proximal portion, a distal portion, and a central longitudinal axis, the flexible elongate member sized and shaped for insertion into human vasculature; and a flow sensing element fixedly secured to the distal portion of the flexible elongate member, wherein the flow sensing element is mounted at an oblique angle with respect to the central longitudinal axis of the flexible elongate member; and a processing unit in communication with the flow-sensing intravascular device, the processing unit configured to: obtain flow measurements from the flow-sensing intravascular device; and output a visual representation of the obtained flow measurements to a display. In some instances, the processing unit is further configured to determine whether the flow sensing element is suitably positioned within a vessel based on the obtained flow measurements. In that regard, the processing unit can be configured to determine whether the flow sensing element is suitably positioned within the vessel based on flow measurements obtained during rotation of the flexible elongate member about the central longitudinal axis. In some instances, the processing unit is further configured to provide a visual indication to the user as to whether the flow sensing element is suitably positioned within the vessel. The processing unit can be further configured to provide a visual indication to the user as to an amount of rotation of the flexible elongate member about the central longitudinal axis to cause the flow sensing element to be suitably positioned within the vessel.

In some instances, a method of evaluating a vessel of a patient is provided that includes obtaining a flow-sensing intravascular device, the flow-sensing intravascular device including: a flexible elongate member having a proximal portion, a distal portion, and a central longitudinal axis, the flexible elongate member sized and shaped for insertion into human vasculature; and a flow sensing element fixedly secured to the distal portion of the flexible elongate member, wherein the flow sensing element is mounted at an oblique angle with respect to the central longitudinal axis of the flexible elongate member; introducing the flow-sensing intravascular device into a vessel of a patient; and utilizing the flow-sensing intravascular device to obtain flow measurements from within the vessel of the patient. The method can also include rotating the flow-sensing intravascular device to orient the flow sensing element away from a wall of the vessel.

Other devices, systems, and methods specifically configured to interface with such devices and/or implement such methods are also provided.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
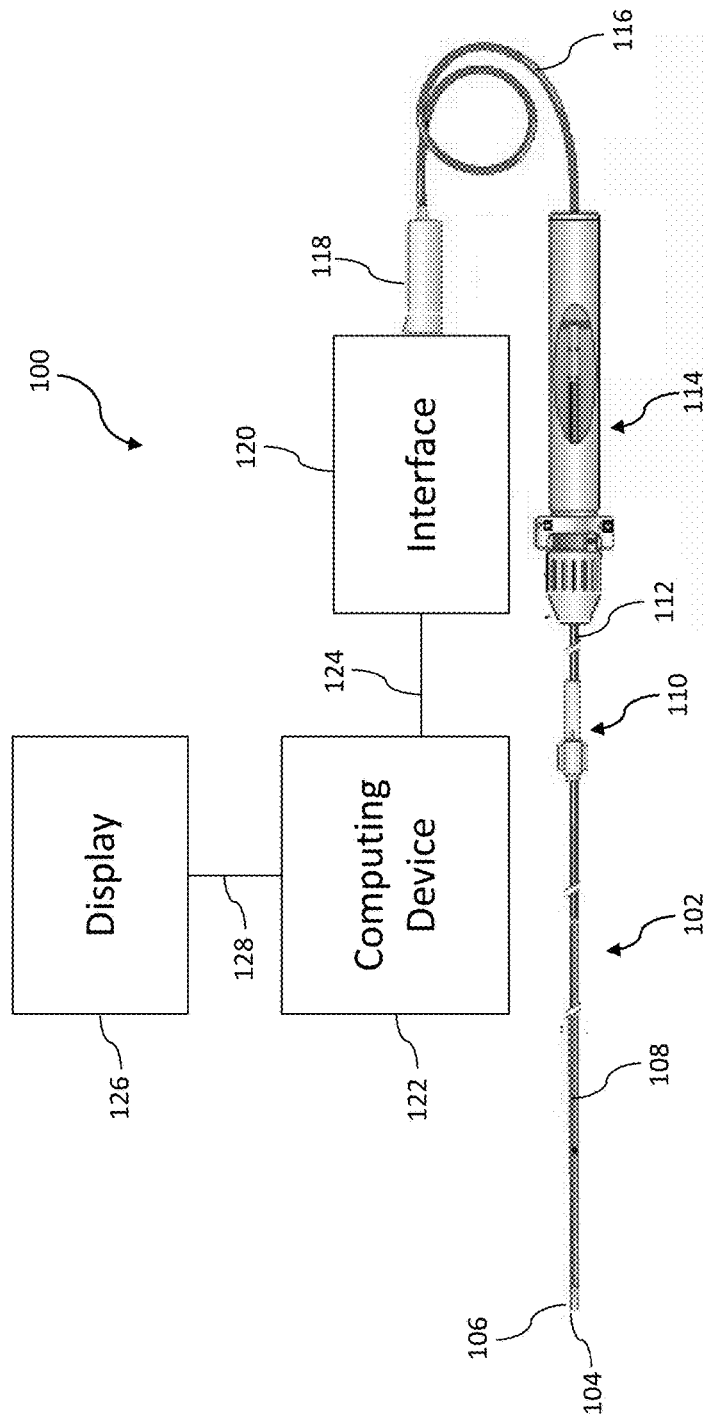
FIG. 1 is a diagrammatic, schematic view of a system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, shown therein is a system 100 according to an embodiment of the present disclosure. In that regard, FIG. 1 is a diagrammatic, schematic view of the system 100. As shown, the system 100 includes an instrument 102. In that regard, in some instances instrument 102 may be any form of device, instrument, or probe sized and shaped to be positioned within a vessel. In the illustrated embodiment, instrument 102 is generally representative of a guide wire. In other embodiments, instrument 102 may be a catheter, including a rapid-exchange catheter or an over-the-wire catheter.

The instrument 102 is configured to obtain diagnostic information about a vessel in which the instrument is positioned. In that regard, the instrument 102 includes one or more sensors, transducers, and/or other monitoring elements configured to obtain the diagnostic information about the vessel. The diagnostic information includes one or more of flow (velocity), flow (volume), pressure, images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 102 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 104 of the instrument 102 in some instances. In some instances, at least one of the one or more sensors, transducers, and/or other monitoring elements is positioned at the distal tip 104 of the instrument 102.

The instrument 102 includes at least one element configured to monitor flow within a vessel. The flow monitoring element can take the form of an ultrasound transducer. For example, in some instances the flow monitoring element is an ultrasound transducer configured to detect Doppler shifts in blood flow. In some instances, the flow monitoring element includes a vortex flow sensor as described in "A MEMS-Based Vortex Flow Sensor for Aggressive Media," Nicholas Pedersen, Per E Andersen (2003), *Proceedings of IEEE Sensors* 2003 (IEEE Cat. No. 03CH37498) 1 p. 320-325, which is hereby incorporated by reference in its entirety. In some instances, the flow monitoring element includes a thermoelectric (thermodilution) flow sensor as described in "A Novel Flexible Thermoelectric Sensor for Intravascular Flow Assessment," Arjen van der Horst, Dennis van der Voort, Benjamin Mimoun, Marcel C M Rutten, Frans N van de Vosse, Ronald Dekker (2013), *JSEN_IEEE Sensors Journal (JSEN)* XX (XX) p. 1-1, which is hereby incorporated by reference in its entirety. In some instances, the flow monitoring element includes a sensor as described in "A Wireless Microsensor for Monitoring Flow and Pressure in a Blood Vessel Utilizing a Dual-Inductor Antenna Stent and Two Pressure Sensors," Kenichi Takahata, Andrew D DeHennis, Kensall D Wise, Yogesh B Gianchandani (2004), *MEMS_IEEE International Conference on Micro Electro Mechanical Systems (MEMS)* p. 216-219, which is hereby incorporated by reference in its entirety. In some instances, magnetic resosnance imaging (MRI) is utilized to monitor flow within the vessel as described in "Assessment of Coronary Flow Reserve with Fast Cine Phase Contrast Magnetic Resonance Imaging: Comparison With Measurement by Doppler Guide Wire," M Shibata, H Sakuma, N Isaka, K Takeda, C B Higgins, T Nakano (1999), *JMRI_Journal of Magnetic Resonance Imaging (JMRI)* 10 (4) p. 563-568, which is hereby incorporated by reference in its entirety. In some instances, the flow monitoring element includes an optical flow sensor, such as those described in "Characterization of a Low-Cost Optical Flow Sensor When Using an External Laser as a Direct Illumination Source," Davinia Font, Marcel Tresanchez, Tomas Palleja, Merce Teixido, Jordi Palacin (2011), *Sensors* 11 (12) p. 11856-70, which is hereby incorporated by reference in its entirety. In some instances, the flow monitoring element includes a magnetostrictive sensor, such as those described in "*Development of a Bio-Inspired Magnetostrictive Flow and Tactile Sensor*, Michael Adam Marana (2012), which is hereby incorporated by reference in its entirety.

In some instances, the instrument 102 includes at least one pressure monitoring element in addition to the flow monitoring element. In that regard, the pressure monitoring element can be a piezo-resistive pressure sensor, a piezoelectric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. An example of a commercially available guide wire product that includes both flow and pressure monitoring elements is the ComboWire® XT pressure and flow guide wire available from Volcano Corporation. Generally, the instrument 102 is sized such that it can be positioned through a vessel without significantly impacting fluid flow through the vessel that could impact the flow readings. Accordingly, in some instances the instrument 102 has an outer diameter of 0.018" or less. In some embodiments, the instrument 102 has an outer diameter of 0.014" or less.

In the illustrated embodiment, the instrument 102 is a guide wire having a distal tip 104 and a housing 106 positioned adjacent the distal tip. The housing 106 is configured to house one or more sensors, transducers, and/or other monitoring elements configured to obtain the diagnostic information about the vessel. In the illustrated embodiment, the housing 156 contains at least a flow sensor configured to monitor a flow within a lumen in which the instrument 102 is positioned. A shaft 108 extends proximally from the housing 106. A torque device 110 is positioned over and coupled to a proximal portion of the shaft 108. A proximal end portion 112 of the instrument 102 is coupled to a connector 114. A cable 116 extends from connector 114 to a connector 118. In some instances, connector 118 is configured to be plugged into an interface 120. In that regard, interface 120 is a patient interface module (PIM) in some instances. In some instances, the cable 116 is replaced with a wireless connection. In that regard, it is understood that various communication pathways between the instrument 102 and the interface 120 may be utilized, including physical connections (including electrical, optical, and/or fluid connections), wireless connections, and/or combinations thereof.

The interface 120 is communicatively coupled to a computing device 122 via a connection 124. Computing device 122 is generally representative of any device suitable for performing the processing and analysis techniques discussed within the present disclosure. In some embodiments, the computing device 122 includes a processor, random access memory, and a storage medium. In that regard, in some particular instances the computing device 122 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 122 is a console device. In some particular instances, the computing device 122 is similar to the s5™ Imaging System or the s5i™ Imaging System, each available from Volcano Corporation. In some instances, the computing device 122 is portable (e.g., handheld, on a rolling cart, etc.). Further, it is understood that in some instances the computing device 122 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 114, cable 116, connector 118, interface 120, and connection 124 facilitate communication between the one or more sensors, transducers, and/or other monitoring elements of the instrument 102 and the computing device 122. However, this communication pathway is exemplary in nature and should not be considered limiting in any way. In that regard, it is understood that any communication pathway between the instrument 102 and the computing device 122 may be utilized, including physical connections (including electrical, optical, and/or fluid connections), wireless connections, and/or combinations thereof. In that regard, it is understood that the connection 124 is wireless in some instances. In some instances, the connection 124 includes a communication link over a network (e.g., intranet, internet, telecommunications network, and/or other network). In that regard, it is understood that the computing device 122 is positioned remote from an operating area where the instrument 102 is being used in some instances. Having the connection 124 include a connection over a network can facilitate communication between the instrument 102 and the remote computing device 122 regardless of whether the computing device is in an adjacent room, an adjacent building, or in a different state/country. Further, it is understood that the communication pathway between the instrument 102 and the computing device 122 is a secure connection in some instances. Further still, it is understood that, in some instances, the data communicated over one or more portions of the communication pathway between the instrument 102 and the computing device 122 is encrypted.

The display 126 is communicatively coupled to the computing device 122 via a connection 128. Similar to the connection 124 between interface 120 and the computing device 122, it is understood that any communication pathway between the display 126 and the computing device 122 may be utilized, including physical connections (including electrical, optical, and/or fluid connections), wireless connections, and/or combinations thereof. In that regard, it is understood that the connection 128 is wireless in some instances. In some instances, the connection 128 includes a communication link over a network (e.g., intranet, internet, telecommunications network, and/or other network). In that regard, it is understood that the computing device 122 is positioned remote from the display 126 in some instances. Having the connection 128 include a connection over a network can facilitate communication between the display 126 and the remote computing device 122 regardless of whether the computing device is in an adjacent room, an adjacent building, or in a different state/country.

It is understood that one or more components of the system 100 are not included, are implemented in a different arrangement/order, and/or are replaced with an alternative device/mechanism in other embodiments of the present disclosure. For example, in some instances, the system 100 does not include interface 120. In such instances, the connector 118 (or other similar connector in communication with instrument 102) may plug into a port associated with computing device 122. Alternatively, the instrument 102 may communicate wirelessly with the computing device 122. Generally speaking, the communication pathway between the instruments 102 and the computing device 122 may have no intermediate nodes (i.e., a direct connection), one intermediate node between the instrument and the computing device, or a plurality of intermediate nodes between the instrument and the computing device.

Figure 2:
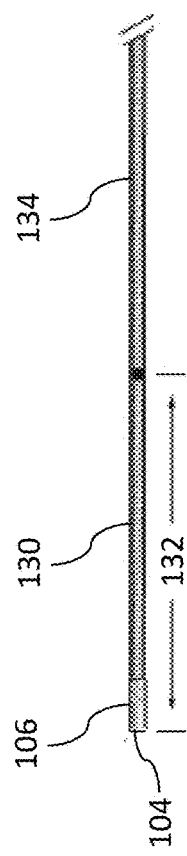
FIG. 2 is a diagrammatic, side view of a distal portion of an intravascular device according to an embodiment of the present disclosure.

Referring now to FIG. 2, shown therein is a diagrammatic, side view of a distal portion of an intravascular device according to an embodiment of the present disclosure. As shown, the distal portion includes a flexible element 130 extending proximally from the housing 106 positioned adjacent the distal tip 104. In that regard, the flexible element 130 and the housing 106 define a distal working section of the instrument 102 that extends a distance 132 from the distal tip 104. In some instances, the distance 132 is between 3 cm and 30 cm, with some embodiments being approximately 27 cm. The flexible element 130 can include one or more coils, polymer tubes, and/or coil-embedded polymer tubes. A main body 134 of the instrument 102 extends proximally from the flexible element 130 to a proximal portion of the instrument 102.

Figure 3:
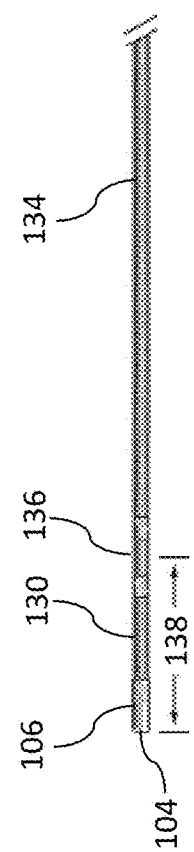
FIG. 3 is a diagrammatic, side view of a distal portion of an intravascular device according to another embodiment of the present disclosure.

Referring now to FIG. 3, shown therein is a diagrammatic, side view of a distal portion of an intravascular device according to another embodiment of the present disclosure. As shown, the distal portion includes a flexible element 130 extending proximally from the housing 106 positioned adjacent the distal tip 104. A sensing element 136 is coupled to the proximal end of the flexible element 130. The sensing element 136 can include a housing or not. The sensing element 136 can be a pressure sensor, imaging element, flow sensor, and/or other element configured to obtain data from within a vessel. The sensing element 136 is spaced from the distal tip 104 of the instrument 102 by a distance 138. In some instances, the distance 138 is between 1 cm and 10 cm, with some embodiments being approximately 3 cm. In some instances, an additional flexible element is positioned proximal of the sensing element 136 between the main body 134 and the sensing element 136. In that regard, the flexible element 130 and/or the flexible element proximal of the housing 136 can include one or more coils, polymer tubes, and/or coil-embedded polymer tubes.

Figure 4:
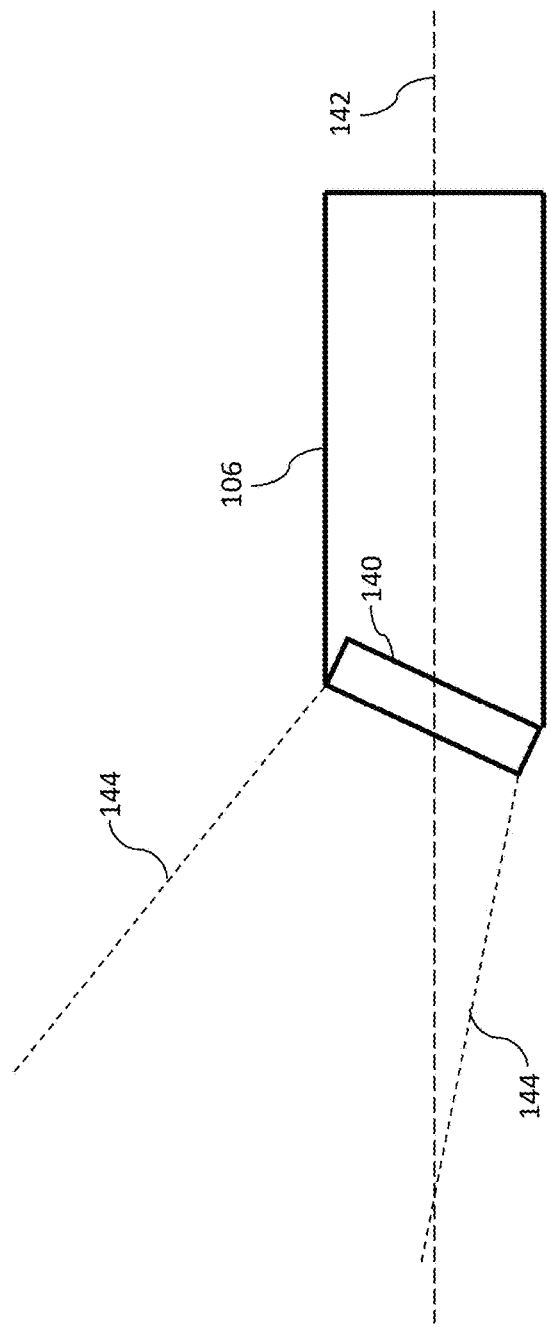
FIG. 4 is a diagrammatic, side view of a distal portion of an intravascular device according to an embodiment of the present disclosure.
Figure 5:
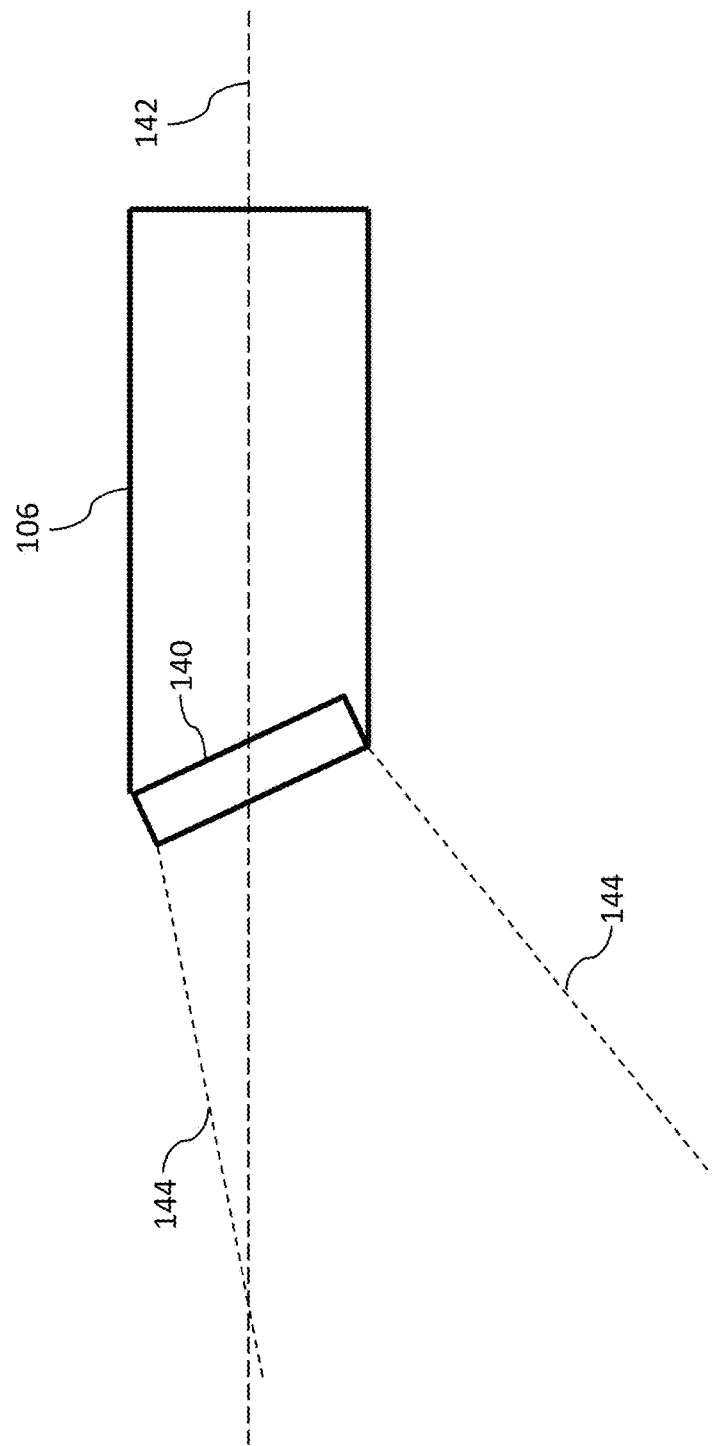
FIG. 5 is a diagrammatic, side view of the distal portion of the intravascular device of FIG. 4, but showing the intravascular device rotated one-hundred eighty degrees about a central longitudinal axis of the intravascular device relative to orientation of FIG. 4 according to an embodiment of the present disclosure.

Referring now to FIG. 4, shown therein is a diagrammatic, side view of a distal portion of an intravascular device according to an embodiment of the present disclosure. A flow sensing element 140 is mounted within the distal portion of the housing 106. As shown, the flow sensing element 140 is mounted at an oblique angle with respect to a central longitudinal axis 142 of the instrument 102. The flow sensing element 140 can be mounted at any suitable oblique angle relative to the central longitudinal axis 142, including between about 1 degree and about 89 degrees, between about 10 degrees and about 60 degrees, and between about 20 degrees and about 40 degrees. Accordingly, in situations where the flow sensing element 140 is an ultrasound transducer, the wave path 144 of the ultrasound transducer will likewise extend at the oblique angle relative to the central longitudinal axis 142, as shown in FIG. 4. As a result, rotation of the instrument 102 about the central longitudinal axis 142 can be utilized to change the orientation of the wave path 144 of the flow sensing element 140 relative to surrounding anatomical structure(s). In that regard, FIG. 5 illustrates the orientation of the flow sensing element 140 after the instrument 102 has been rotated about the central longitudinal axis 142 one hundred and eighty degrees. As shown in FIG. 5, the wave path 144 extends in the opposite direction relative to the central longitudinal axis 142 when compared to the orientation of FIG. 4.

As a result of this ability to change the orientation of the wave path 144 of the flow sensing element 140 relative to surrounding anatomical structure(s) by rotating the instrument 102 about the central longitudinal axis 142 (e.g., by using torque device 110), the flow sensing element 140 can be easily repositioned to obtain improved flow measurements in situations where the distal tip of the instrument 102 rests against and/or is directed towards a vessel wall.

Figure 6:
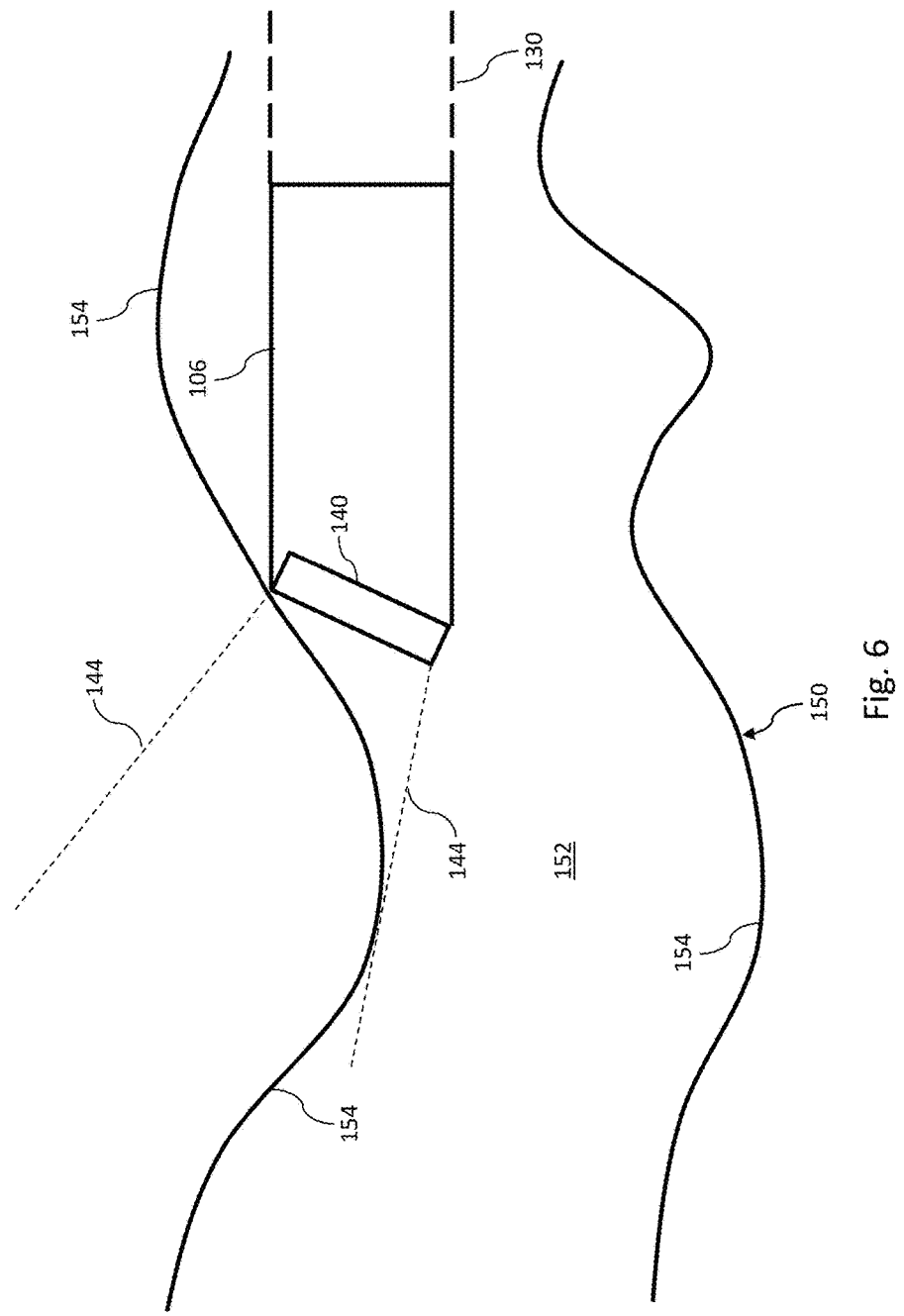
FIG. 6 is a diagrammatic, partial cross-sectional side view of a distal portion of an intravascular device positioned within a vessel according to an embodiment of the present disclosure.
Figure 7:
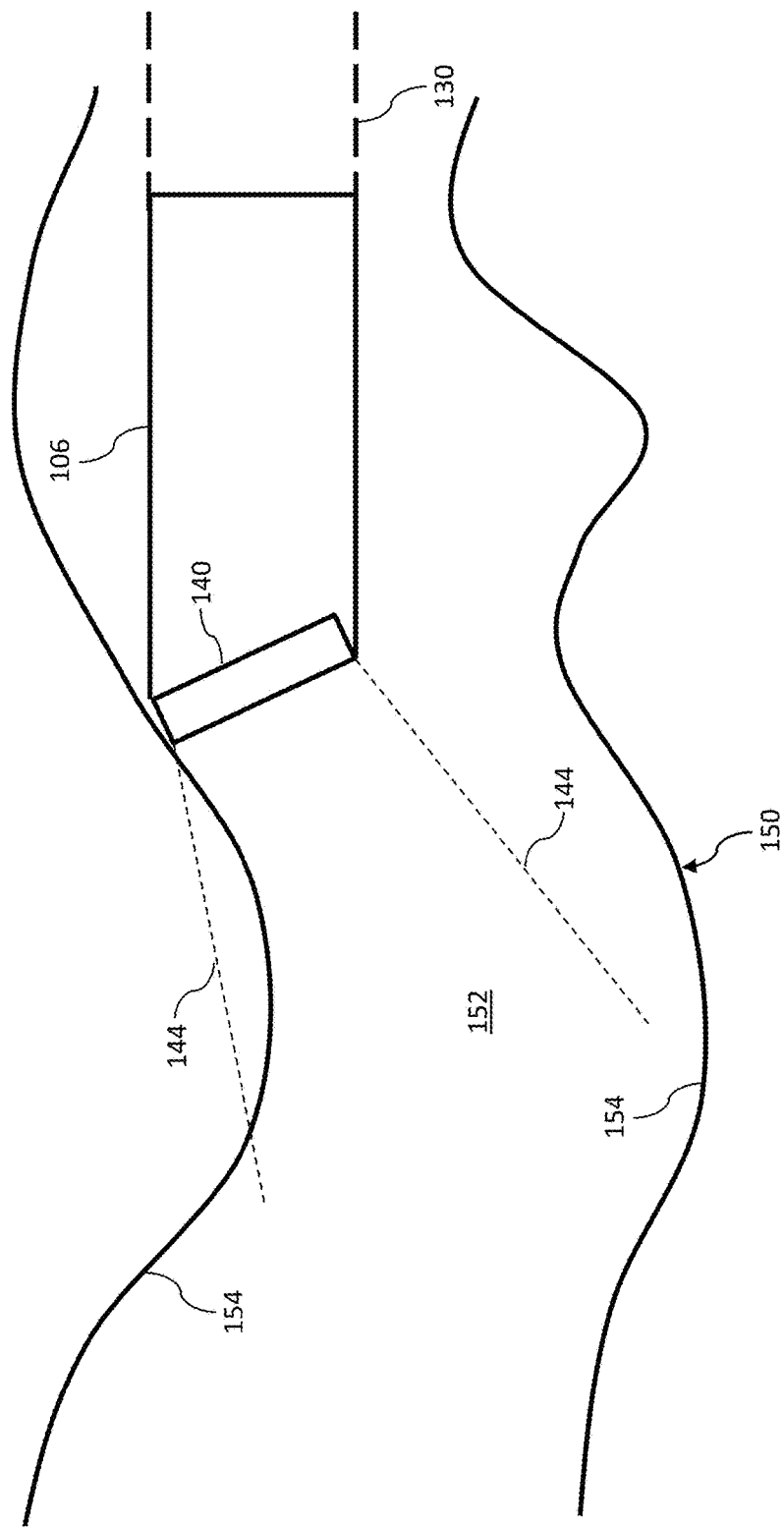
FIG. 7 is a diagrammatic, partial cross-sectional side view of the distal portion of the intravascular device positioned within the vessel of FIG. 6, but showing the intravascular device rotated one-hundred eighty degrees about a central longitudinal axis of the intravascular device relative to the orientation of FIG. 6 according to an embodiment of the present disclosure.

For example, referring now to FIGS. 6 and 7, shown therein are diagrammatic, partial cross-sectional side views of the distal portion of an intravascular device positioned within a vessel according to aspects of the present disclosure. In that regard, FIG. 6 shows the instrument 102 positioned within a vessel 150 having a vessel lumen 152 and surrounding vessel walls 154. In the orientation of FIG. 6, the flow sensing element 140 is positioned adjacent to and directed towards the vessel wall 154. As a result, any flow measurements obtained by the flow sensing element 140 will have little diagnostic value. However, by simply rotating the instrument 102 one-hundred eighty degrees about the central longitudinal axis 142 of the instrument, the flow sensing element 140 will be reoriented to the position shown in FIG. 7 such that it is directed more towards the center of the vessel lumen 152. As a result, the flow sensing element 140 is suitably positioned within the vessel 150 to obtain flow measurements of diagnostic value.

In some instances, the instrument 102 is in communication with a processing unit, such as computing device 122, that is configured to obtain flow measurements from the flow-sensing instrument 102 and output a visual representation of the obtained flow measurements to a display. Further, in some instances the processing unit is further configured to determine whether the flow sensing element 140 is suitably positioned within the vessel 150 based on the obtained flow measurements. For example, the processing unit may compare the obtained flow measurements to an expected or threshold value. If the obtained measurements meet or exceed the expected/threshold value, then the flow sensing element 140 is suitably positioned. However, if the obtained measurements do not meet or exceed the expected/threshold value, then the flow sensing element 140 is not suitably positioned. In some instances, the processing unit provides a visual indication to the user via the display as to whether the flow sensing element is suitably positioned within the vessel.

In some instances, the processing unit is configured to determine whether the flow sensing element is suitably positioned within the vessel based on flow measurements obtained during a rotation of the instrument 102 about the central longitudinal axis 142. For example, the processing unit can monitor obtain flow measurements as the instrument 102 is rotated to different positions about the central longitudinal axis 142. One or more rotary encoders or other suitable rotational monitor(s) can be utilized to communicate the relative rotational position to the processing unit. By monitoring the relative changes in the flow measurements associated with the different rotational positions of the instrument 102, suitable and/or optimal rotational orientations of the instrument 102 for obtaining flow measurements from within the vessel can be identified. In that regard, the improved flow measurements can be associated with improved orientation of the flow sensing element 140 relative to the vessel lumen 152. To that end, in some instances the processing unit is further configured to provide a visual indication to the user via the display as to the amount of rotation of the flexible elongate member necessary to cause the flow sensing element to be suitably and/or optimally positioned within the vessel to obtain diagnostically relevant flow measurements.

Figure 8:
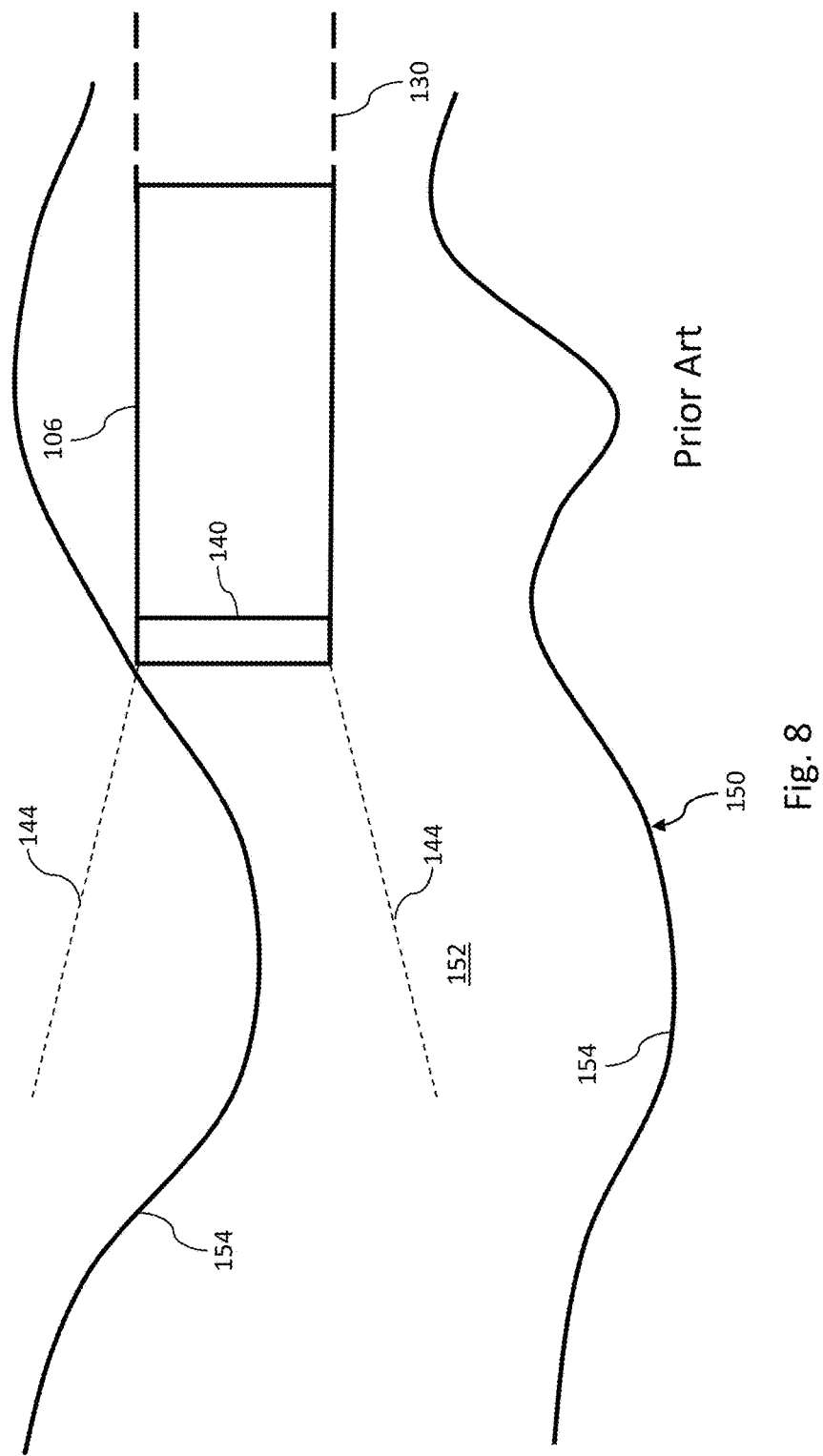
FIG. 8 is a diagrammatic, partial cross-sectional side view of a distal portion of an intravascular device positioned within a vessel according to another embodiment of the present disclosure.

In contrast to the embodiments of the present disclosure, FIG. 8 shows that with a conventional prior art device having the flow sensing element 140 mounted perpendicular to the longitudinal axis 142 of the instrument 102, rotation of the instrument will not change the orientation of the flow sensing element. Rather, the flow sensing element 140 will remain positioned adjacent to and directed towards the vessel wall 154, as shown in FIG. 8, regardless of the rotational position of the instrument. Accordingly, the surgeon or other user of the flow sensing intravascular device would need to advance or retract the device longitudinally through the vessel and then return the device back to the desired region of interest in the hope that the distal tip of the device would settle in a different, better orientation. Such movement can cause the instrument 102 to lose a desired longitudinal orientation within the vessel such that it is no longer be positioned in the desired region of interest, which can increase procedure time as the user attempts to reestablish the desired position. Further, the repositioning may still result in the flow sensing element being positioned in an unsuitable orientation with respect to the vessel wall 154 for obtaining flow measurements of diagnostic value. Accordingly, it may take multiple repositionings before the flow sensing element is properly positioned.

Figure 9:
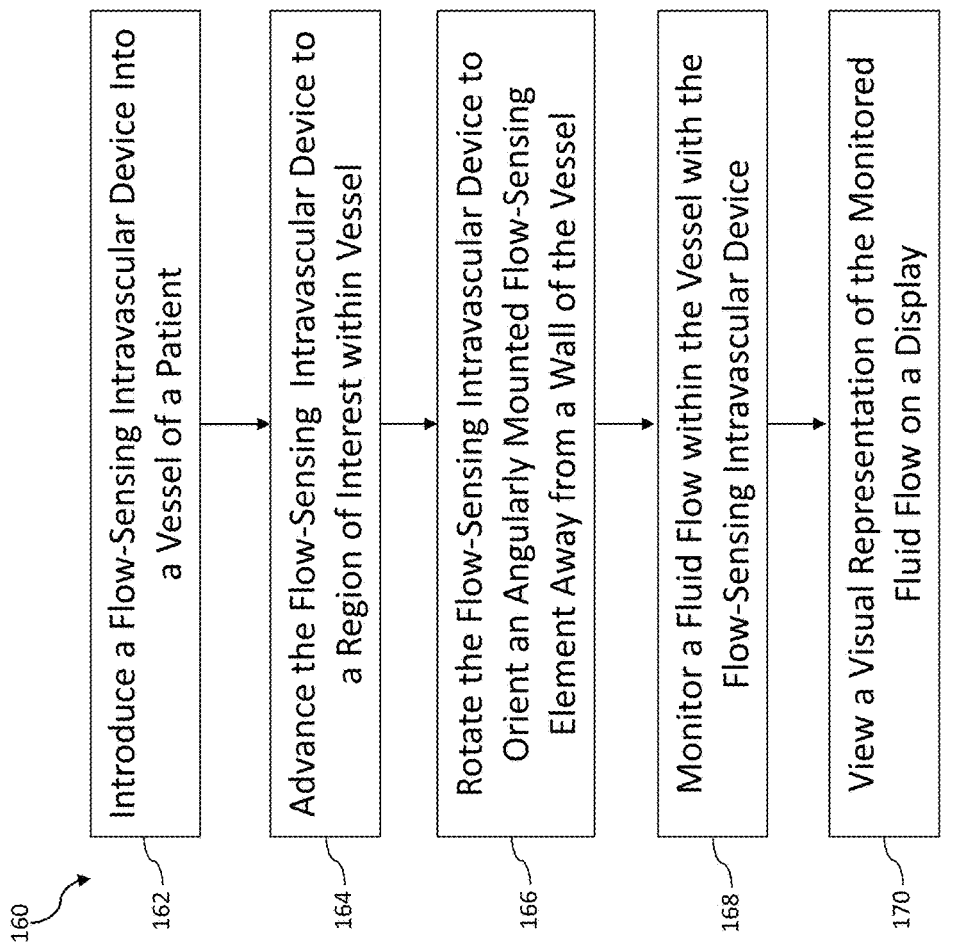
FIG. 9 is a flow chart illustrating steps for evaluating a vessel of a patient according to an embodiment of the present disclosure.

Referring now to FIG. 9, shown therein is a flow chart illustrating steps for evaluating a vessel of a patient according to an embodiment of the present disclosure. In particular, the method 160 includes, at step 162, introducing a flow sensing intravascular device into a vessel of a patient. The flow sensing intravascular device can be similar to those described above. In particular, the flow sensing intravascular device can include a flow sensing element mounted at an oblique angle with respect to the central longitudinal axis of the device. At step 164, the method 160 includes advancing the flow sensing intravascular device to a region of interest within the vessel. In some instances, the positioning of the flow sensing intravascular device relative to the region of interest is tracked using angiography and one or more radiopaque markers on the distal portion of the flow sensing intravascular device.

Further, the radiopaque markers can be utilized to facilitate co-registration of the flow measurements obtained with the intravascular device to corresponding images of the vessel, including angiography, x-ray, CT scans, IVUS, OCT, and/or other imaging modalities. In some implementations, co-registration is performed as disclosed in one or more of U.S. Pat. No. 7,930,014, titled "VASCULAR IMAGE CO-REGISTRATION," U.S. Provisional Patent Application No. 61/747,480, titled "SPATIAL CORRELATION OF INTRA-VASCULAR IMAGES AND PHYSIOLOGICAL FEATURES" and filed Dec. 31, 2012, U.S. Provisional Patent Application No. 61/856,509, titled "DEVICES, SYSTEMS, AND METHODS FOR ASSESSMENT OF VESSELS" and filed Jul. 19, 2013, and U.S. Provisional Patent Application No. 61/895,909, titled "DEVICES, SYSTEMS, AND METHODS FOR VESSEL ASSESSMENT" and filed Oct. 25, 2013, each of which is hereby incorporated by reference in its entirety.

At step 164, the method 160 includes rotating the flow sensing intravascular device to orient the angularly mounted flow sensing element away from a wall of the vessel. As discussed above, in some instances a processing unit in communication with the flow sensing intravascular device provides visual indications to the user via a display as to whether the intravascular device and, in particular, the flow sensing element is suitably positioned within the vessel for obtaining diagnostically relevant flow measurements. At step 168, the method 160 includes monitoring the fluid flow within the vessel with the flow sensing intravascular device. At step 170, the method includes viewing a visual representation of the monitored fluid flow on the display.

The method 160 can include additional steps, omit steps, reorder the steps, and/or otherwise be modified without departing from the scope of the present disclosure. For example, as noted above, in some instances the flow sensing intravascular device can further include a pressure sensing element. As a result, the method 160 can include additional steps associated with processing flow and/or pressure measurements. For example, an intravascular device with both a pressure sensing and a flow sensing capabilities provides a desirable environment in which to calculate fractional flow reserve (FFR) or other pressure ratio calculations using pressure readings, and coronary flow reserve (CFR) using flow readings. The ability to measure and compare both the pressure and velocity flow and create an index of hyperemic stenosis resistance significantly improves the diagnostic accuracy of this ischemic testing. It has been shown that distal pressure and velocity measurements, particularly regarding the pressure drop-velocity relationship such as Fractional Flow reserve (FFR), Coronary flow reserve (CFR) and combined P-V curves, reveal information about the stenosis severity. For example, in use, the intravascular device may be advanced to a location on the distal side of the stenosis. The pressure and flow velocity may then be measured at a first flow state. Then, the flow rate may be significantly increased, for example by the use of drugs such as adenosine, and the pressure and flow measured in this second, hyperemic, flow state. The pressure and flow relationships at these two flow states are then compared to assess the severity of the stenosis and provide improved guidance for any coronary interventions. The ability to take the pressure and flow measurements at the same location and same time with the same intravascular device can improve the accuracy of these pressure-velocity loops and, therefore, improve the accuracy of the diagnostic information.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system comprising:
a flow-sensing intravascular device that includes:
a flexible elongate member having a proximal portion, a distal portion terminating at a distal tip, and a central longitudinal axis, the flexible elongate member sized and shaped for insertion into human vasculature;
a flow sensing element secured to the distal tip of the flexible elongate member, wherein the flow sensing element is fixedly mounted in a forward facing manner at an oblique angle with respect to the central longitudinal axis of the flexible elongate member;
a pressure sensing element spaced from the flow sensing element and secured to the flexible elongate member proximal to the flow sensing element; and
a rotational monitor configured to determine a rotational position of the flow sensing element; and
a processing unit in communication with the flow-sensing intravascular device and the rotational monitor, the processing unit configured to:
obtain flow measurements from the flow-sensing intravascular device;
determine whether the flow sensing element is oriented toward a wall of a vessel based on the obtained flow measurements;
receive, from the rotational monitor, a communication of the rotational position of the flow sensing element;
output a visual representation of the obtained flow measurements to a display; and
output a visual indication to the display indicating an amount of rotation of the flexible elongate member to cause the flow sensing element to be oriented away from the wall of the vessel, wherein the amount is based on the communication of the rotational position of the flow sensing element provided by the rotational monitor.

2. The system of claim 1, wherein the oblique angle is between about 10 degrees and about 60 degrees.

3. The system of claim 2, wherein the oblique angle is between about 20 degrees and about 40 degrees.

4. The system of claim 1, wherein the flow sensing element is an ultrasound transducer.

5. The system of claim 4, wherein the ultrasound transducer is configured to detect Doppler shifts in blood flow.

6. The system of claim 1, wherein the processing unit is further configured to determine whether the flow sensing element is suitably positioned within a vessel based on a comparison of the obtained flow measurements to a threshold value.

7. The system of claim 1, wherein the flow-sensing intravascular device further comprises a connector coupled to the proximal portion of the flexible elongate member, wherein the connector is in communication with the flow sensing element.

8. The system of claim 1, wherein the flexible elongate member has an outer diameter of 0.018" or less.

9. The system of claim 8, wherein the flexible elongate member has an outer diameter of approximately 0.014".

10. The system of claim 1, wherein the processing unit is configured to determine whether the flow sensing element is suitably positioned within the vessel based on a comparison of a plurality of flow measurements obtained at a plurality of rotational positions during rotation of the flexible elongate member about the central longitudinal axis.

11. The system of claim 10, wherein the processing unit is further configured to provide a visual indication to the user as to whether the flow sensing element is at a suitable rotational position of the plurality of rotational positions within the vessel.

12. The system of claim 10, wherein the rotational monitor comprises a rotary encoder configured to determine and communicate the rotational position of the flow sensing element for each of a plurality of angular positions to the processing unit, and wherein the processing unit is configured to compare relative changes in the plurality of flow measurements at each of the plurality of angular positions.

* * * * *